(12) United States Patent
Uihlein et al.

(10) Patent No.: US 8,617,177 B2
(45) Date of Patent: Dec. 31, 2013

(54) WIRE BASKET UNIT HAVING FIXING DISK ELEMENT

(75) Inventors: Bernhard Uihlein, Dettingen (DE); Gerard Louis Florent Torchio, Verrieres le Buisson (FR)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 12/935,285

(22) PCT Filed: Apr. 1, 2008

(86) PCT No.: PCT/EP2008/002600
§ 371 (c)(1),
(2), (4) Date: Dec. 22, 2010

(87) PCT Pub. No.: WO2009/121379
PCT Pub. Date: Oct. 8, 2009

(65) Prior Publication Data
US 2011/0112547 A1    May 12, 2011

(51) Int. Cl.
*A61B 17/24* (2006.01)
(52) U.S. Cl.
USPC .......................................................... 606/113
(58) Field of Classification Search
USPC .................................. 606/113, 114, 127, 128
See application file for complete search history.

(56) References Cited

U.S. PATENT DOCUMENTS

| | | | |
|---|---|---|---|
| 4,198,960 A | 4/1980 | Utsugi | |
| 5,057,114 A | 10/1991 | Wittich et al. | |
| 5,064,428 A | 11/1991 | Cope et al. | |
| 5,344,427 A | 9/1994 | Cottenceau et al. | |
| 5,725,525 A | 3/1998 | Kordis | |
| 5,989,266 A | 11/1999 | Foster | |
| 6,224,612 B1 | 5/2001 | Bates et al. | |
| 7,101,379 B2 * | 9/2006 | Gregory et al. | 606/127 |
| 7,824,415 B2 * | 11/2010 | Teague et al. | 606/127 |
| 2003/0088254 A1 * | 5/2003 | Gregory et al. | 606/127 |
| 2006/0058813 A1 * | 3/2006 | Teague et al. | 606/113 |
| 2007/0106304 A1 * | 5/2007 | Hammack et al. | 606/113 |

FOREIGN PATENT DOCUMENTS

| | | |
|---|---|---|
| DE | 10117836 | 7/2002 |
| DE | 10150399 | 4/2003 |
| DE | 102005030010 | 12/2006 |
| WO | 02078632 | 10/2002 |

\* cited by examiner

*Primary Examiner* — Tuan V Nguyen
(74) *Attorney, Agent, or Firm* — Coloplast Corp., Coloplast A/S; Nick Baumann

(57) ABSTRACT

A wire basket includes a fixing disc element coupled with several wire strands. The wire strands extend between a front end of the wire basket and a rear end of the wire basket to define an orbital shape. The fixing disc element forms a front closure of the wire basket and has at least first and second through-openings. A first of the wire strands is formed from a first wire segment that is looped through the first of the through-openings of the fixing disc element along a path extending from the rear end of the wire basket forward through the fixing disc element to form a U-shaped deflection that is looped through a separate second of the through-openings of the fixing disc element along a path extending from the fixing disc element to the rear end of the wire basket.

11 Claims, 4 Drawing Sheets

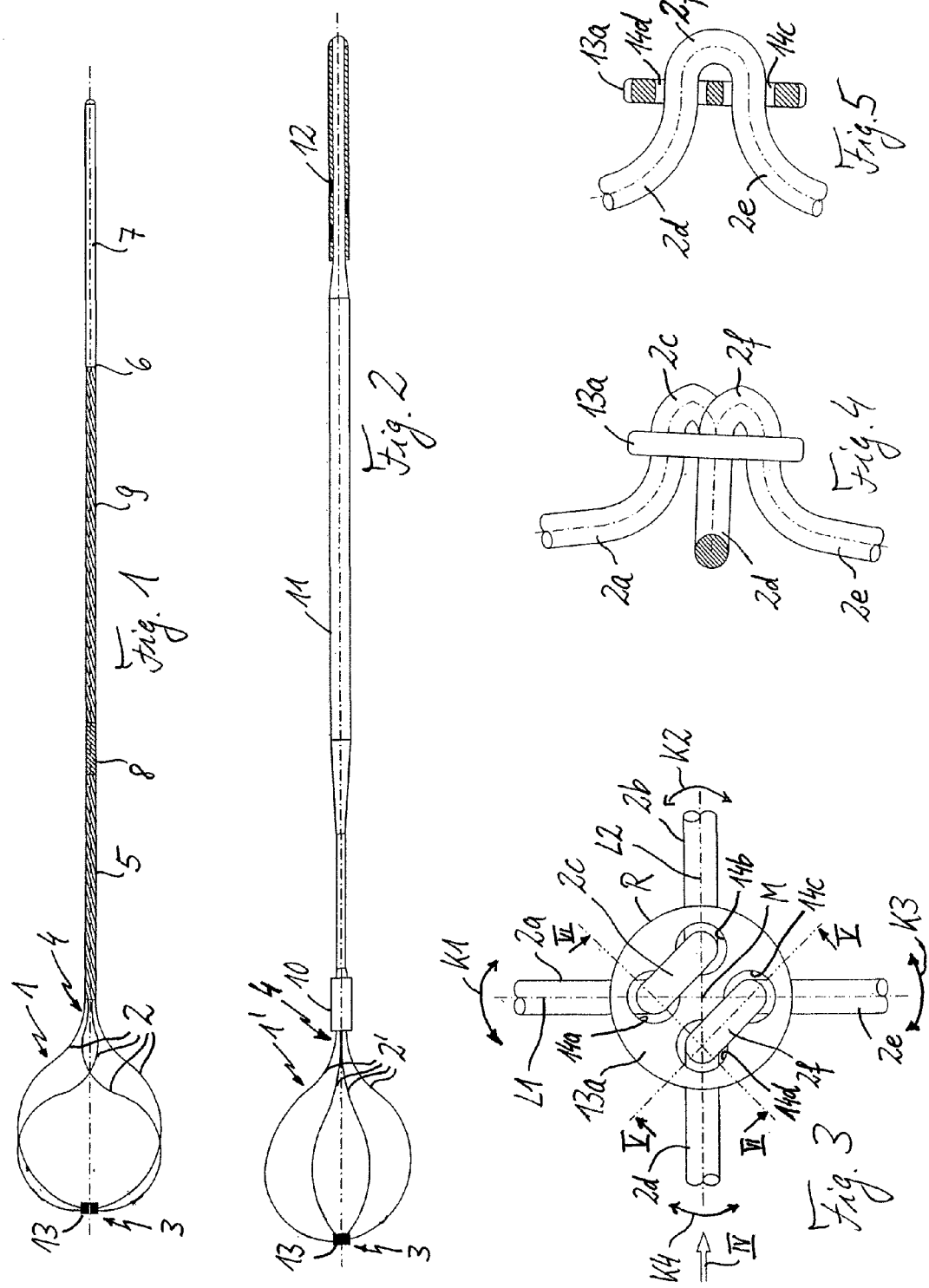

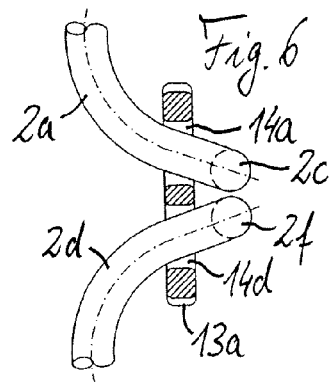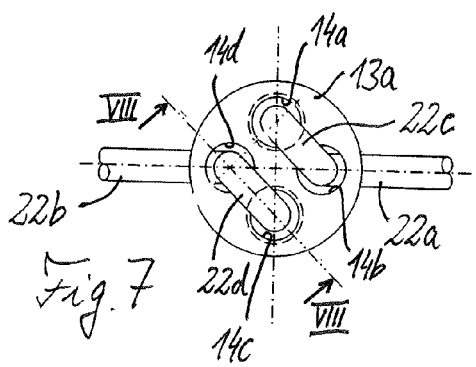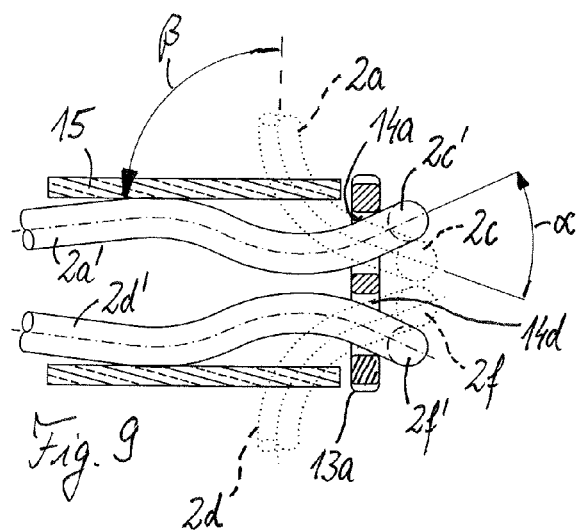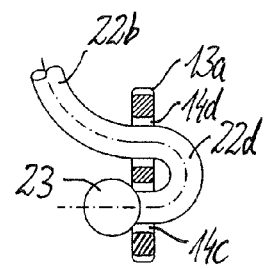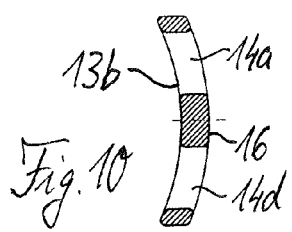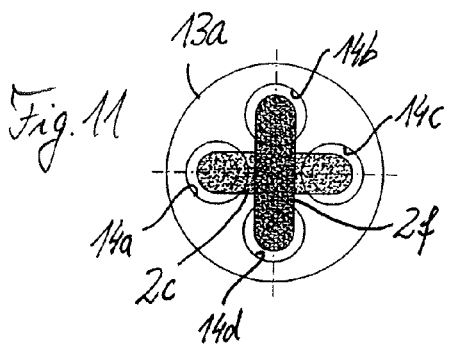

WIRE BASKET UNIT HAVING FIXING DISK ELEMENT

Figure 12:
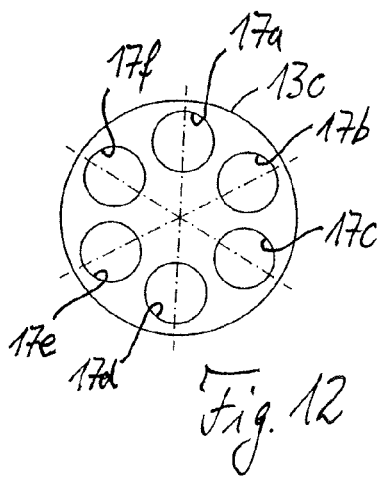

The invention relates to a wire basket unit, in particular for a medical wire basket instrument, with a balloon-shaped wire basket composed of several wire strands which extend between a front end of the wire basket and a rear end of the wire basket and are formed from one or more wire segments, and a fixing disc element on which the wire strands are fixed at the front end of the wire basket so as to form a front closure of the wire basket, wherein the fixing disc element has at least two through-openings.

A wire basket unit of this kind is disclosed in laid-open application DE 101 50 399 A1 for a medical instrument. Such medical instruments are used, for example, as stone-retrieving basket instruments and as polypectomy snare instruments. In these uses, the balloon-shaped wire basket can be drawn, folding up, into a receiving sleeve and can be moved back out of the latter again, unfolding. Upon insertion into the receiving sleeve, a permanent deformation of the wire strands forming the basket must be avoided, and, during use, for example for retrieving stones located in human or animal tissue cavities, the risk of perforating the tissue must be minimized. In order to tackle the latter problem, it is often desired to design the balloon-shaped wire basket with a substantially tipless front end ("tipless basket"). In order to meet these demands, DE 101 50 399 A1 proposes the use of a ring element or of a holed disc element with one or more through-openings through which the wire segments are looped once and, forming an eyelet, are fixed on the ring element or the holed disc element. When using a holed disc element, the latter is preferably provided with peripheral indentations, in order to create space there for receiving the wire segments forming the eyelet.

The technical problem addressed by the invention is that of making available a wire basket unit of the type mentioned at the outset which, compared to the abovementioned prior art, is further improved in terms of the fixing of the wire strands by the fixing disc element at the front end of the wire basket.

The invention solves this problem by making available a wire basket unit having the features of Claim 1. In this wire basket unit, at least a first of the wire strands is formed from a first wire segment which is looped through a first of the through-openings of the fixing disc element from the rear forwards and, forming a U-shaped deflection, is looped through a second of the through-openings of the fixing disc element from the front to the rear again and is thus fixed on the fixing disc element.

Tests carried out in practice have shown that the resulting fixing of the wire strands on the fixing disc element, provided for this purpose with several through-openings, is surprisingly advantageous in terms of the problems discussed in the introduction and in particular also in terms of the reproducible folding-together and unfolding of the balloon-shaped wire basket and the good stability of the wire basket in the deployed state. The U-shaped looping of the wire segment through two separate through-openings of the fixing disc element permits, on the one hand, the mobility of the wire strand fixation on the fixing disc element, which mobility is desired and necessary for the folding-together of the wire basket, and avoids, on the other hand, too loose a fixation, which can lead, for example, to undesired twisting and therefore tilting of the wire basket.

In a development of the invention according to Claim 2, at least two of the wire strands forming the wire basket are formed from a one-piece wire segment which is deflected in a U-shape on the fixing disc element and is looped through two associated through-openings and from there extends rearwards, in each case with a wire segment section forming one of the wire strands of the basket, at least as far as the rear end of the wire basket. In this way, at least two of the basket-forming wire strands can be made available from one wire segment. In a further embodiment of this measure according to Claim 3, several pairs of wire strands are in this way formed from in each case a one-piece wire segment.

Depending on the particular use, the through-openings can have suitable cross-sectional shapes, of which some advantageous configurations according to the invention are specified in Claim 4. Depending on the particular requirements, the through-openings can have identical or different cross-sectional shapes.

In a further embodiment of the invention according to Claim 5, the through-openings are arranged at the same distance from a centre point and are equidistant about the circumferential direction of the fixing disc element. This is advantageous, for example, for the provision of wire baskets in which the wire strands are arranged equidistant in the circumferential direction of the wire basket.

In one embodiment of the invention according to Claim 6, at least two wire segments are looped through at least one of the through-openings. This measure can in particular be combined with a suitably adapted cross-sectional configuration of this through-opening, e.g. a configuration in the shape of an oblong hole. In this way, when necessary, the number of through-openings in the fixing disc element can be smaller than the number of basket-forming wire strands.

In the embodiment of the invention according to Claim 7, the wire strands are fixed on the fixing disc element without intersecting. This can be of advantage, for example, in terms of achieving identical deflection conditions and therefore identical fixation conditions for all the wire strands in corresponding uses. Alternatively, an intersecting deflection of at least two wire strands on the fixing disc element can also be provided.

In an advantageous development of the invention according to Claim 8, at least one wire segment, in its deflection area, i.e. on the front side of the fixing disc element opposite the actual wire basket area, extends in a non-parallel, i.e. twisted, longitudinal plane compared to the longitudinal plane in which at least one associated wire strand extends in the basket-forming section between the front and rear ends of the wire basket. It has been found that this fixing measure is very favourable in respect of sufficient mobility of the fixing site on the one hand and in respect of sufficient stability, in particular stability against twisting, of the fixing site.

In a development of the invention according to Claim 9, the fixing disc element has a shape that curves forwards to its central area, for example a cup shape. This design measure can have positive effects on the desired mobility of the fixing site for the respective wire strand and can provide a transition of the front wire basket closure that is adapted to the balloon shape of the adjoining wire basket area.

Figure 13:
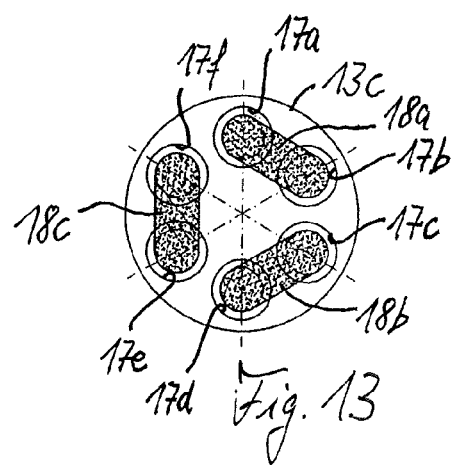
Figure 14:
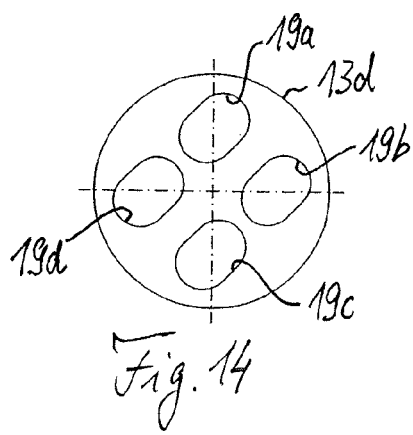
Figure 15:
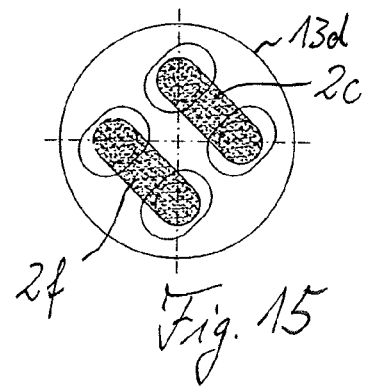
Figure 16:
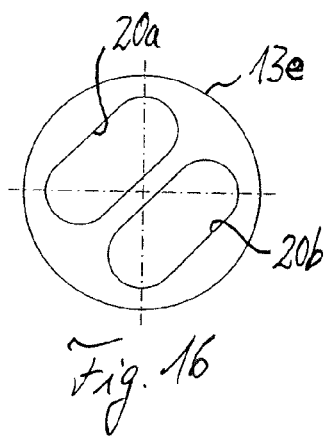
Figure 17:
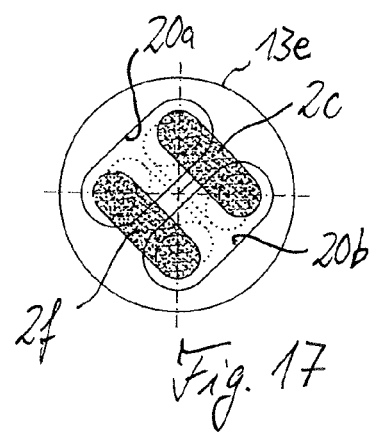
Figure 18:
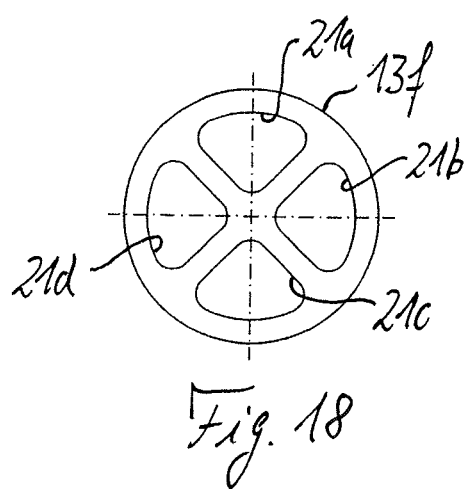
Figure 19:
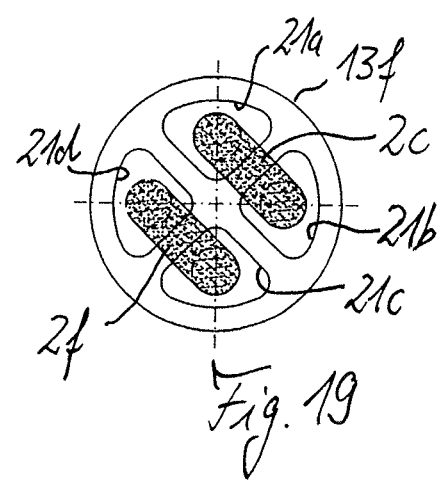

Advantageous embodiments of the invention are described below and are depicted in the drawings, in which:

FIG. 1 shows a side view of a medical wire basket unit with a balloon-shaped wire basket made of wire strands continued into a shaft area and with a wire-fixing element at the front end, FIG. 2 shows a side view of a variant of the medical wire basket unit from FIG. 1, in which the wire strands forming the wire basket are gathered at the rear end of the wire basket in a receiving element, FIG. 3 shows a plan view of the front area of the wire basket from FIG. 1 or 2, with a flat four-hole fixing disc element as wire-fixing element, FIG. 4 shows a side view of the front area of the wire basket from FIG. 3 along an arrow IV in FIG. 3, FIG. 5 shows a sectional view along a line V-V in FIG. 3, FIG. 6 shows a sectional view along a line VI-VI in FIG. 3, FIG. 7 shows a plan view, corresponding to FIG. 3, of a variant with a wire basket composed of two individual wire strands, FIG. 8 shows a sectional view along a line VIII-VIII in FIG. 7, FIG. 9 shows a sectional view of the front area of the wire basket from FIG. 3 in a state in which the wire basket is drawn into a receiving sleeve, FIG. 10 shows a longitudinal sectional view of a modified, curved fixing disc element, FIG. 11 shows a plan view of a front wire basket closure, modified in relation to FIG. 3, with intersecting wire segments looped through, FIG. 12 shows a plan view of a fixing disc element which is modified in relation to that in FIG. 3 and which has six through-openings, FIG. 13 shows a plan view of the fixing disc element from FIG. 12 with three wire segments looped through, FIG. 14 shows a view, corresponding to FIG. 12, of a modified fixing disc element with four through-openings shaped as oblong holes, FIG. 15 shows the view from FIG. 14, with two wire segments looped through, FIG. 16 shows a view, corresponding to FIG. 12, of a further modified fixing disc element with two through-openings shaped as oblong holes, FIG. 17 shows the view from FIG. 16, with two wire segments looped through, FIG. 18 shows a view, corresponding to FIG. 12, of a further modified fixing disc element with four sector-shaped through-openings, and FIG. 19 shows the view from FIG. 18, with two wire segments looped through.

FIGS. 1 and 2 show two wire basket units of the kind that can be used in medical instruments, in particular in stone-retrieving basket instruments or polypectomy snare instruments. The wire basket unit in FIG. 1 has a balloon-shaped wire basket 1 composed of four wire strands 2 which, to form the balloon-shaped wire basket 1, extend from a front end 3 of the wire basket to a rear end 4 of the wire basket 1 and which, to form a front shaft section 5, are continued rearwards in a twisted configuration as far as a coupling site 8, where they are connected by a welded join to an adjacent central twisted shaft section 9 which can be formed from a continuation of these wire strands or from its own wire strands. At a transition point 6, the central shaft section 9 merges into a rear shaft section 7, which is composed of a solid core wire material.

The wire basket unit in FIG. 2 analogously has four wire strands 2' which, in order to form a balloon-shaped wire basket 1', extend between a front end 3 of the wire basket and a rear end 4 of the wire basket. In this illustrative embodiment, the wire strands 2' are gathered at their rear end in a receiving sleeve 10. In this wire basket unit, the shaft is composed of a solid core wire 11, which tapers via a conical section into a front area adjacent to the receiving sleeve 10 and tapers via a conical section into a rear area. A sheath is fitted over the rear tapered area of the core wire 11.

The main point of interest here is the design of the wire basket unit at the front end 3 of the basket, where the wire strands 2, 2' forming the basket are brought together and fixed on a fixing element 13 and in this way connected to one another. To achieve the desired balloon shape for the wire basket 1, 1', and to achieve what is as far as possible a tipless front closure 3 of the wire basket, it is desirable that the wire strands 2, 2' run out from one another in a substantially radial direction as close as possible to the fixing element 13 before they then extend with an increasing axial component to the maximum basket diameter and from there run back together again to the rear end 4 of the basket. The fixing element 13 additionally has the function of fixing the wire strands 2, 2' such that they are sufficiently movable but at the same time not too loose. The mobility of the fixing arrangement is needed in order to ensure a desired elasticity of the wire basket 1, 1' and, in particular in said medical uses, to be able to draw the wire basket unit and wire basket 1, 1', folding up, into a receiving sleeve and thus be able to introduce it into a human or animal tissue channel. At the time of use, the wire basket unit is then pushed out of the receiving sleeve until the wire basket 1, 1' is exposed again and, through the inherent elasticity of the wire strands 2, 2', assumes its deployed operational state shown in FIGS. 1 and 2. Not fixing them too loosely on the fixing element 13 stabilizes the deployed wire basket 1, 1' and in particular avoids undesired twisting, and therefore tilting, of the wire basket 1, 1'.

The invention is distinguished by a particular design of the fixing element 13 and by the manner in which the wire strands 2, 2' are fixed on same, so as to optimally meet these requirements. For this purpose, according to the invention, the fixing element 13 is in the form of a fixing disc element provided with several through-openings. The fixing disc element can also be of any desired shape, e.g. circular, oval, triangular or polygonal, etc. Its thickness, i.e. the dimension in the axial direction, is preferably a multiple smaller than its transverse dimension.

FIGS. 3 to 6 show a first example of such a fixing disc element 13a, as can be used as fixing element 13 for the wire basket unit in FIG. 1 or FIG. 2 or for another wire basket unit with a balloon-shaped wire basket. As is shown, the in this case circular fixing disc element 13a has four through-openings 14a, 14b, 14c, 14d which, in the example shown, are formed at an equidistant 90° angle spacing and approximately at the same distance from a centre point M and from the disc edge R. A first wire strand 2a and a second wire strand 2b are formed from a first one-piece wire segment which, forming a U-shaped deflection area 2c, is looped through two adjacent through-openings 14a, 14b, i.e. the wire segment coming from the rear end of the wire basket forms the first wire strand 2a, is then looped from the rear forwards through the through-opening 14a in the fixing disc element 13a, bends round with the U-shaped section 2c on the front side of the fixing disc element 13a into the second through-opening 14b, passes through the latter, and then, forming the second wire strand 2b, extends back to the rear end of the wire basket. Analogously, a third wire strand 2d and a fourth wire strand 2e of the wire basket are formed in one piece from a second wire segment which, with a U-shaped deflection area 2f, is looped through the two other adjacent through-openings 14c, 14d.

This has the result that each of the two one-piece wire segments provides in each case two adjacent wire strands 2a, 2b and 2d, 2e, respectively, which are offset by 90° in the circumferential direction of the basket. In addition, the two deflection areas 2c, 2f of the wire segments on the front side of the fixing disc element 13a extend without intersecting and in parallel longitudinal planes, like the sectional plane of FIG. 5, which extend non-parallel to the longitudinal planes in which the wire strands 2a, 2b, 2d, 2e extend in their basket-forming area, i.e. a longitudinal plane L1, in which the basket-forming sections of the wire strands 2a and 2e lie, and a longitudinal plane L2, in which the basket-forming sections of the wire strands 2b and 2d lie. In the example shown, the wire segments in the deflection area 2c, 2f extend at an angle of ca. 45° with respect to these two longitudinal planes L1, L2 in which the four basket-forming sections of the wire strands 2a, 2b, 2d, 2e lie, as can be seen from FIG. 3. Depending on the configuration and positioning of the through-openings, it is of course also possible to have any other desired orientations of the U-shaped deflection area(s) of the wire strands or wire segments relative to the course of the wire strand in the basket-forming area.

Although FIGS. 4 to 6 suggest the presence of a tip area, these representations are schematic and not true to scale, and without reference to the extent of the whole wire basket. In real embodiments, the axial extent of the front closure of the wire basket with the fixing disc element 13a and the U-shaped wire deflection areas 2c, 2f is smaller than the wire basket diameter by a multiple or by one or more orders or magnitude. Such designs are usually designated as tipless or virtually tipless.

Tests carried out in practice have shown that, with this type of fixing of the basket-forming wire strands 2a, 2b, 2d, 2e on the fixing disc element 13a, with formation of an approximately tipless front closure of the wire basket, the above-mentioned requirements in terms of sufficient mobility, on the one hand, and sufficient stability and safety against twisting, on the other hand, of the wire strand fixing arrangement at the front end, and thus of the wire basket as a whole, are met surprisingly effectively. This is also attributed in particular to the property whereby each of the wire strands 2a, 2b, 2d, 2e is not only held by being engaged through a through-opening 14a, 14c on the fixing disc element 13a, but is also held by being guided, with a deflection on the front side of the fixing disc element 13, through a second through-opening 14b, 14d.

In the example shown, each wire strand merges into the further wire strand made available in one piece by the same wire segment. In an alternative embodiment, the wire strand ends individually after being guided through its second through-opening, e.g. with formation of a thickened wire end which secures it against disengagement from the through-opening. In this case, two through-openings are then needed for the individual wire strand. FIGS. 7 and 8 illustrate a corresponding illustrative embodiment in which the wire basket is formed from two individual wire strands or wire segments 22a, 22b as a wire snare, where the two basket-forming or snare-forming wire strands 22a, 22b are offset relative to each other by 180° about the longitudinal axis of the basket or snare.

A first wire segment 22a extends, in order to form a first half of the snare, from the rear end of the wire basket or wire snare to the fixing disc element 13a, which is here identical to the one in the illustrative embodiment in FIGS. 3 to 6, through a first 14b of its four through-openings 14a to 14d, is deflected back on the front side of the fixing disc element 13a with a U-shaped section 22c, and is passed rearwards again through a second 14a of the through-openings 14a to 14d of the fixing disc element 13a, in order to end there, on the rear side of the fixing disc element 13a, with a thickened wire end that secures it against disengagement. In the same way, the second wire segment 22b extends, in order to form the second half of the snare, from the rear end of the wire basket forwards to the fixing disc element 13a, and, as can be seen more clearly from FIG. 8, from there through a third 14d of the through-openings 14a to 14d, and is deflected back on the front side of the fixing disc element 13a with a U-shaped deflection area 22d through the fourth 14c of the through-openings 14a to 14d to the rear side of the fixing disc element 13a, where it terminates with a thickened ball-shaped wire end 23 whose external diameter is greater than the diameter of the associated through-opening 14c and thus secures the wire segment 22b against disengagement from the associated through-openings 14c, 14d. It will be appreciated that, in this system design with wire strands each fixed individually on the fixing disc element, it is possible to produce wire basket units having any desired number, including an odd number, of wire strands forming the wire basket, e.g. for wire baskets composed of three or five wire strands.

In other alternative illustrative embodiments, combined forms can be provided in which one or more pairs of wire strands are made available by in each case one wire segment, and at least one wire strand is made available individually from another wire segment. In further alternative embodiments, it is also possible for more than two basket-forming wire strands to be made available from a one-piece wire segment, by means of this wire segment being bent once or several times through 180° at the rear end of the wire and in each instance extending back to the front end of the wire basket.

For the example shown in FIGS. 3 to 6, the aforementioned safety against twisting is symbolized by tilt arrows K1, K2, K3, K4 in FIG. 3. The described fixing of the wire strands on the fixing disc element 13a has the result that the wire basket has a relatively high degree of stiffness against bending loads or twisting loads exerted on the wire strands 2a to 2d in this arrow direction, i.e. against twisting loads exerted on the wire strands 2a to 2d transverse to their longitudinal extent in the basket-forming area. This stiffness and therefore stability of the wire basket is in particular much greater than in an alternative solution in which each wire strand is held only on a single associated through-opening of a corresponding fixing disc element. It is also much greater than in the aforementioned traditional solutions with a ring element as the fixing element. Moreover, the present solution according to the invention means that there is also no need for formation of an eyelet for fixing the wire strands on the fixing disc element, as is the case in the corresponding aforementioned traditional solutions with a holed fixing disc element.

However, in the wire basket unit according to the invention, a mobility of the wire strand fixing arrangement on the fixing disc element 13a is retained, as is needed in order to draw the wire basket into a receiving sleeve and in so doing fold it up. For the illustrative embodiment in FIGS. 3 to 6, this is illustrated in FIG. 9, in a view that corresponds to FIG. 6. On being drawn into a receiving sleeve 15, indicated only by its front part, the wire basket folds up, i.e. the individual wire strands 2a, 2b, 2d, 2e are pressed together in the basket-forming area. The characteristic fixing of the wire strands on the fixing disc element 13a, together with the inherent elasticity of the wire strands 2a, 2b, 2d, 2e, advantageously permits this folding-together of the wire basket.

As can be seen from FIG. 9, the through-openings 14a to 14d in the fixing disc element are formed with an external diameter slightly greater than the diameter of the wire strands 2a, 2b, 2d, 2e, such that the looped-through wire segments with their deflection areas 2c, 2f are able to move to a certain extent in the through-openings 14a to 14d and can thereby resiliently follow the folding or unfolding movement experienced by the wire strands 2a, 2b, 2d, 2e in their basket-forming area. To illustrate this, the course of the two wire strands 2a and 2d in the deployed state of the wire basket, as in FIG. 6, is shown by dotted lines in FIG. 9, compared to the course of these two wire strands, indicated by solid lines, in their basket-forming areas 2a', 2d' and in their deflection area 2c', 2f. As will be seen from this, when the wire basket folds together, the two deflection areas 2c, 2f move radially outwards in a kind of tilting movement by a tilt angle α, for example of ca. 45°, and thus facilitate the radial folding-together of the wire strands in the basket-forming area, where there is a corresponding folding-together tilting movement of each wire strand 2a, 2b, 2d, 2e, in its section adjoining the rear of the fixing disc element 13a, by a fold angle β of ca. 90°. The through-openings 14a to 14d thus serve to some extent as pivot points for this elastic movement of the wire strands and permit the required movement clearance. In this way, the mobility of the wire-fixing arrangement, together with the inherent elasticity and configuration of the wire strands 2a, 2b, 2d, 2e, permits optimal folding-together of the wire basket 1.

FIG. 10 illustrates a variant of the flat fixing disc element 13a shown in the example of FIGS. 3 to 6. This variant comprises a curved configuration, e.g. a cup shape, of a suitably modified fixing disc element 13b, which in other respects corresponds to that of FIGS. 3 to 6, in particular as regards the formation of the four through-openings 14a to 14d, such that, except for this one difference, reference may be made to the above description thereof. In particular, this fixing disc element 13b has a shape that curves distally, i.e. forwards, from a peripheral edge area 15 to a central area 16, and this can have a positive influence on the mobility of the wire strands fixed, as in the example of FIGS. 3 to 6, in the through-openings 14a to 14b. Moreover, this shape of the fixing element disc 13b can improve its shape adaptation to the wire basket area adjoining it from the rear, i.e. from the left in FIG. 10, since the fixing disc element 13b in this way curves in the same direction as the adjoining area of the wire basket.

FIG. 11 shows, in relation to the illustrative embodiment in FIGS. 3 to 6, an alternative looping-through of the two wire segments forming the four wire strands 2a, 2b, 2d, 2e. Whereas the two wire segments in the example in FIGS. 3 to 6 are each looped with their U-shaped deflection areas 2c, 2f through two adjacent openings of the four through-openings 14a to 14d without intersecting, in the example according to FIG. 11 they are looped with intersecting U-shaped deflection areas 2c, 2d through two diametrically opposite openings 14a, 14c and 14b, 14d, respectively, of the four through-openings 14a to 14d. In this case, therefore, each of the two wire segments forms two opposite wire strands, offset by 180° in the circumferential direction of the wire basket, of the four basket-forming wire strands 2a, 2b, 2d, 2e. This intersected fixing of the two wire segments and therefore of the four wire strands 2a, 2b, 2d, 2e on the fixing element disc 13a or on another fixing disc element according to the invention, such as the curved fixing disc element 13b in FIG. 10, can afford advantages for certain applications.

FIGS. 12 to 19 show, on the basis of a number of illustrative embodiments, the high degree of variability in terms of the configuration of the fixing disc element according to the invention, said variability permitting adaptation to the requirements of the particular application. For each example shown, the fixing disc element in question is depicted in a plan view from the front, first without and then with the wire segments looped through it.

FIGS. 12 and 13 show a fixing disc element 13c with six circular through-openings 17a to 17f which are formed in the fixing element disc 13c so as to be equidistant in the circumferential direction. As can be seen from FIG. 13, three wire segments are looped with their U-shaped deflection area 18a, 18b, 18c through in each case two adjacent through-openings 17a and 17b, 17c and 17d, and 17e and 17f, respectively, and thus in each case form two circumferentially adjacent wire strands of a balloon-shaped wire basket composed in this way of six wire strands. A narrow-mesh wire basket of this kind with six wire strands is of advantage in certain applications. It will be appreciated that in this example too of a wire basket composed of six wire strands, it is possible, as an alternative to the non-intersecting looping-through of the wire segments shown in FIG. 13, to also provide an intersecting looping-through of at least two of the three wire segments, in analogy to the illustrative embodiment in FIG. 11, e.g. where each of the three wire segments is in each case looped through two diametrically opposite openings of the six through-openings 17a to 17f.

FIGS. 14 and 15 illustrate a fixing disc element 13d which corresponds to the fixing disc element 13a of FIGS. 3 to 6, with the modification that the through-openings have a slightly oblong shape. The fixing disc element 13d specifically has four oblong openings 19a to 19d whose longer main axis runs perpendicular to the orientation of the U-shaped deflection area 2c, 2f of the two wire segments which, as in the example of FIGS. 3 to 6, are looped through without intersecting. The slight oblong shape of the through-openings 19a, 19b can, if so desired, increase the mobility of the two wire segments thus fixed, which form the four wire strands of the wire basket, which wire strands, in a manner not shown in FIG. 15 and corresponding to the example of FIG. 3, extend radially upwards, downwards, to the right and to the left from the fixing disc element 13d and axially rearwards.

FIGS. 16 and 17 illustrate a fixing disc element 13e in which two through-openings 20a, 20b are formed with a pronounced oblong shape, in this case with each through-opening 20a, 20b receiving two wire segments or wire strands. As can be seen from FIG. 17, the U-shaped deflection areas 2c, 2f of the two wire strands, which make available the four basket-forming wire strands, are specifically looped through each of the two oblong through-openings 20a, 20b without intersecting. The pronounced oblong shape of the two through-openings 20a, 20b can, for certain uses, further increase the mobility of the wire strand fixation on this fixing disc element 13e compared to the illustrative embodiments described above.

FIGS. 18 and 19 illustrate a fixing disc element 13f which, like the fixing disc element 13a of FIG. 3, has four through-openings 21a to 21d which are arranged equidistant in the circumferential direction but which, in this example, have the shape of a rounded sector of a circle, as indicated. Once again, as in the example of FIGS. 3 to 6, the two wire segments or the four wire strands formed by them are fixed on this fixing disc element 13f with non-intersecting U-shaped deflection areas 2c, 2f that lie parallel to each other. Depending on the cross-sectional extent of the sector-shaped through-openings 21a to 21d compared to the cross section of the looped-through wire segments, it is also possible in this embodiment, as in the preceding illustrative embodiments, to adjust the mobility of the fixation of the wire strands on the fixing disc element 13f to the desired extent. Alternatively, in the illustrative embodiment according to FIGS. 18 and 19, it is also possible, as in the example of FIG. 11, to have an intersected fixing of the wire strands.

Although the illustrated fixing disc elements 13a to 13f each have a circular shape, it will be understood that the fixing disc element according to the invention can, where necessary, have any other desired edge shape, e.g. oval or the form of a polygon or also an asymmetrical shape. Irrespective of its outer shape, the fixing disc element according to the invention has, in the manner of a button, at least two through-openings for fixing at least one of the wire strands forming the basket. Generally, all the wire strands that form the balloon-shaped wire basket of the wire basket unit according to the invention are in this way fixed on the fixing disc element by being looped through two through-openings with a U-shaped deflection. However, this is not essential. Combined forms can also be used in which this type of fixing is provided only for some of the wire strands forming the wire basket. In most cases, it is advantageous for two or more of the basket-forming wire strands to be made available from a common wire segment in the manner shown and described. However, this too is not essential, and instead it is possible, when necessary, that at least one of the wire strands, after the U-shaped deflection and looping through the second associated through-opening, ends on the rear side of the fixing disc element, e.g. in the form of a ball-shaped thickened wire end, which secures it against disengagement from the through-opening.

Irrespective of the specific configuration, the wire basket unit according to the invention, by virtue of the specific and above-described manner by which the wires are fixed on the fixing disc element provided with through-openings, has an optimized front closure of the wire basket of the balloon-shaped wire basket in terms of mobility, on the one hand, and in terms of stability, on the other hand. In combination with the use of highly flexible wire material for the basket-forming wire strands, the wire basket unit according to the invention permits a reliable and reproducible folding-together of the wire basket when it is drawn into a receiving sleeve and, conversely, a reliable and functionally safe unfolding of the wire basket as it moves out of the receiving sleeve. The folding or unfolding movement is assisted by the material-specific elasticity of the wire strands and by the specific fixing of the wire strands on the fixing disc element which, for example, can be chosen such that the basket-forming wire strands, when folding together and also when unfolding, execute a slight tilting movement at the fixing point, as is explained above with reference to FIG. 9. At the same time, the specific fixing of the wire strands in each case in two through-openings on the fixing disc element avoids excessive twisting of the wire basket, which could lead, for example, to undesired tilting of the wire basket.

As has been mentioned, the wire basket according to the invention can be used in particular in medical instruments, for example in stone-retrieving basket instruments and polypectomy snare instruments. However, the wire basket unit according to the invention can of course also be used in any other desired applications in which there is a need for a flexible, balloon-shaped wire basket.

The invention claimed is:

1. A wire basket comprising:
several wire strands that extend between a front end of the wire basket and a rear end of the wire basket to define an orbital shape formed from one or more wire segments of the wire strands, and
a fixing disc element coupled with the wire strands at the front end of the wire basket to form a front closure of the wire basket, wherein the fixing disc element has at least a first through-opening, a second through-opening, a third through-opening, and a fourth through-opening;
wherein at least a first of the wire strands is formed from a first wire segment that is looped through the first of the through-openings of the fixing disc element along a path extending from the rear end of the wire basket forward through the fixing disc element to form a first U-shaped deflection that is looped through the second of the through-openings of the fixing disc element along a path extending from the fixing disc element to the rear end of the wire basket;
wherein at least a second of the wire strands is formed from a second wire segment that is looped through the third of the through-openings of the fixing disc element along a path extending from the rear end of the wire basket forward through the fixing disc element to form a second U-shaped deflection that is looped through the fourth of the through-openings of the fixing disc element along a path extending from the fixing disc element to the rear end of the wire basket;
wherein the first and second U-shaped deflections are disposed on a distal side of the fixing disc element at the front end of the wire basket, and the first and second U-shaped deflections extend without intersecting in substantially parallel longitudinal planes.

2. The wire basket according to claim 1, further characterized in that each of the several wire strands is formed from a one-piece wire segment that is looped through one through-opening and through a different second through-opening.

3. The wire basket according to claim 1, further characterized in that at least one of the through-openings is formed in the shape of one of a circle, an oblong hole, and a sector of a circle.

4. The wire basket according to claim 1, further characterized in that the through-openings are arranged equidistant from a centre point of the fixing disc element.

5. The wire basket according to claim 1, further characterized in that the fixing disc element has a non-planar curved shape.

6. The wire basket according to claim 1, wherein the first of the wire strands has a section through the fixing disc that is parallel to a longitudinal axis of the wire basket.

7. The wire basket according to claim 6, wherein the section through the fixing disc that is parallel to the longitudinal axis of the wire basket is that portion that is along the path extending from the rear end of the wire basket forward through the fixing disc element.

8. The wire basket according to claim 6, wherein the section through the fixing disc that is parallel to the longitudinal axis of the wire basket is that portion that is looped through the second of the through-openings of the fixing disc element along the path extending from the fixing disc element to the rear end of the wire basket.

9. A wire basket comprising:
several wire strands that extend between a front end of the wire basket and a rear end of the wire basket to define an orbital shape formed from one or more wire segments of the wire strands, and
a fixing disc element coupled with the wire strands at the front end of the wire basket to form a front closure of the wire basket, wherein the fixing disc element has at least a first through-opening, a second through-opening, a third through-opening and a fourth through-opening;
wherein one wire strand is looped through the first of the through-openings of the fixing disc element along a path extending from the rear end of the wire basket forward through the fixing disc element to form a U-shaped deflection that is looped through the second of the through-openings of the fixing disc element along a path extending from the fixing disc element to the rear end of the wire basket, and wherein a second wire strand is looped through the third of the through-openings of the fixing disc element along a path extending from the rear end of the wire basket forward though the fixing disc element to form a second U-shaped deflection that is looped though the fourth of the through-openings of the fixing disc element along a path extending from the fixing disc element to the rear end of the wire basket;

wherein the first and second U-shaped deflections are disposed on a distal side of the fixing disc element at a distal-most portion of the front end of the wire basket, and the first and second U-shaped deflections extend without intersecting and in substantially parallel longitudinal planes.

10. The wire basket of claim 9, wherein the first and second wire strands form four wire segments that extend from the fixing disc element such that two adjacent wire segments are offset by 90° in a circumferential direction of the wire basket.

11. A wire basket comprising:
several wire strands that extend between a front end of the wire basket and a rear end of the wire basket to define an orbital shape formed from one or more wire segments of the wire strands, and
a fixing disc element coupled with the wire strands at the front end of the wire basket to form a front closure of the wire basket, wherein the fixing disc element has at least a first through-opening, and a second through-opening; wherein at least a first of the wire strands is looped through the first of the through-openings of the fixing disc element along a path extending from the rear end of the wire basket forward through the fixing disc element to form a U-shaped deflection that is looped through the second of the through-openings of the fixing disc element along a path extending from the fixing disc element to the rear end of the wire basket, and wherein the first wire strand or a second wire strand is looped through the first of the through-openings of the fixing disc element along a path extending from the rear end of the wire basket forward though the fixing disc element to form a second U-shaped deflection that is looped though the second of the through-openings of the fixing disc element along a path extending from the fixing disc element to the rear end of the wire basket;
wherein the first and second U-shaped deflections are disposed on a distal side of the fixing disc element at a distal-most portion of the front end of the wire basket, and the first and second U-shaped deflections extend without intersecting and in parallel longitudinal planes.

* * * * *